Figure 1:
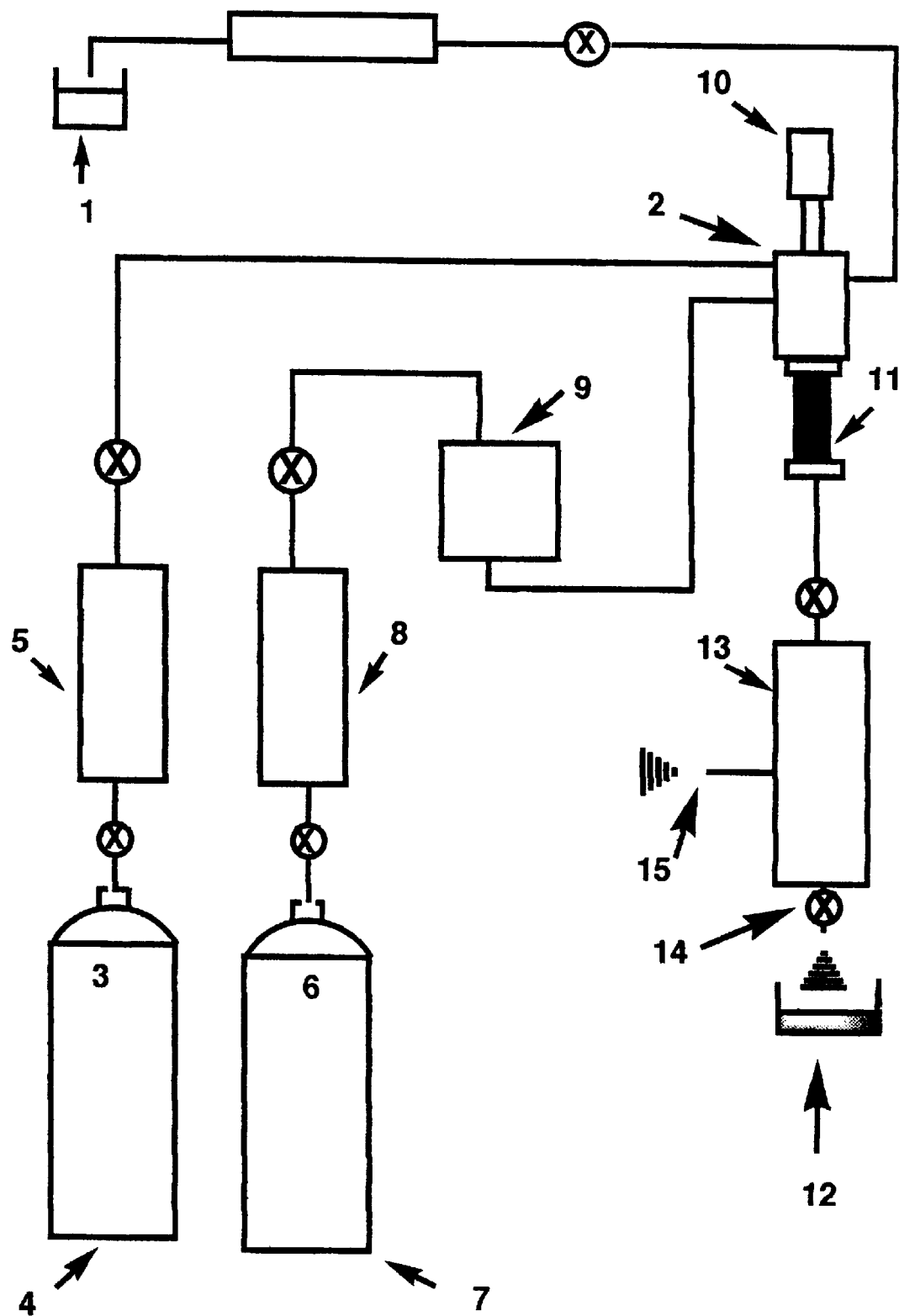

United States Patent [19]
Poliakoff et al.

[11] Patent Number: 6,156,933
[45] Date of Patent: Dec. 5, 2000

[54] SUPERCRITICAL HYDROGENATION

[75] Inventors: Martyn Poliakoff, Beeston; Thomas M. Swan, Bedburn, both of United Kingdom; Thomas Tacke, Paducah, Germany; Martin G. Hitzler, Tachertiny, Ky.; Stephen K. Ross, Consett, United Kingdom; Stefan Wieland, Offfenbach, Germany

[73] Assignees: Degussa-Huls AG, Frankfurt am Main, Germany; Thomas Swan & Co. Ltd., Durham, United Kingdom

[21] Appl. No.: 09/155,660

[22] PCT Filed: Apr. 11, 1997

[86] PCT No.: PCT/GB97/01014

§ 371 Date: Feb. 18, 1999

§ 102(e) Date: Feb. 18, 1999

[87] PCT Pub. No.: WO97/38955

PCT Pub. Date: Oct. 23, 1997

[30] Foreign Application Priority Data

Apr. 17, 1996 [GB] United Kingdom .................. 9607917

[51] Int. Cl.$^7$ .......................... C07C 209/00; C07C 37/00; C07C 5/00
[52] U.S. Cl. .......................... 564/416; 564/420; 564/448; 564/449; 568/799; 568/835; 568/880; 568/881; 585/250; 585/263; 585/264; 585/266
[58] Field of Search .................................... 564/416, 420, 564/448, 449; 508/799, 835, 880, 881; 585/250, 263, 264, 266

[56] References Cited

U.S. PATENT DOCUMENTS 3,969,382  7/1976  Zogel .

Primary Examiner—Paul J. Killos
Attorney, Agent, or Firm—Bromberg & Sunstein LLP

[57] ABSTRACT

Process for the selective hydrogenation of alphatic or aromatic substrates under supercritical or near critical conditions. Hydrogenation is effected using a heterogeneous catalyst in a continuous flow reactor containing a supercritical or near critical reaction medium and selectively of product formation is achieved by varying one or more of the temperature, pressure, catalyst and flow rate.

19 Claims, 7 Drawing Sheets

SUPERCRITICAL HYDROGENATION

The present invention relates to a method of hydrogenating organic compounds. More specifically the present invention relates to heterogeneous catalytic hydrogenation of organic compounds under conditions of continuous flow of the reactants in a continuous flow reactor. The hydrogenation is performed under supercritical or near-critical conditions.

Hydrogenation is a commercially very significant process and enjoys widespread use in the food industry to produce amongst other things edible oils and spreads, and in the fine chemicals, plastics, pharmaceuticals and agricultural industries as a synthetic tool.

Although the use of supercritical fluids as reaction media has been disclosed for a limited number of synthetic organic reactions, the synthetic uses disclosed so far have involved heterogeneous or homogeneous batch systems or homogeneous continuous flow systems and suffer a number of disadvantages.

Catalytic hydrogenation under supercritical conditions is known from WO 94/06738 which discloses a process for manufacturing alcohols by liquid phase heterogeneous catalytic hydrogenation of mono- or dicarboxylic acids or their esters in a liquid inert hydrogen carrier such as a hydrocarbon. In this patent, hydrogenation is preferably carried out under supercritical conditions and is performed in a fixed-bed reactor or a batch autoclave. The process requires a high ratio of hydrogen with respect to the material to be hydrogenated and this is achieved by decreasing the concentration of the starting material in the reaction medium. The alcohol product is separated from dissolved hydrogen on depressurising the mixture. The presence of such an excess of hydrogen presents an explosion risk and is therefore unacceptable for large scale synthesis, unless of course the quantity of carboxylic acid is decreased to such an extent that the amount of hydrogen present does not pose a significant risk. However in this case the quantity of carboxylic acid which can be hydrogenated renders the process useless for large scale synthesis.

The Journal of the American Chemical Society 190495, 117 (31), 8277 discloses asymmetric catalytic hydrogenation reactions in supercritical carbon dioxide using a homogenous chiral rhodium catalyst in a batch-type process. A small-scale reactor is charged with the compound to be hydrogenated and carbon dioxide at a pressure of approximately 3000 psig and hydrogen gas at 200 psig. Significant enantiomeric excesses are claimed for hydrogenations performed under these conditions but the product nevertheless requires purification to separate the catalyst from the product after reaction.

EP-A-0652202 discloses a method for producing formic acid or formic acid derivatives in a reaction employing carbon dioxide in the supercritical state as the reaction medium. The reaction may be performed in the presence of a homogeneous or heterogeneous catalyst. In this patent, the supercritical carbon dioxide medium represents one of the reactants and is consumed during the process. The carbon dioxide is mixed with hydrogen at a relatively high pressure to produce formic acid, or with an active hydrogen group-containing compound to produce a formic acid derivative in a continuous process.

A method for the direct oxidation of benzene or other aromatic hydrocarbons into phenols is disclosed in WO 9420444. In this method, the aromatic hydrocarbon is dissolved in a mixture of supercritical carbon dioxide, molecular oxygen, and hydrogen as a reducing gas. The oxidation is performed under pressure in the presence of a palladium-containing catalyst and the reaction mixture is homogenous, hence avoiding the use of an inefficient 2-phase system. The carbon dioxide separated from the reaction mixture is vaporised and may be re-used in the oxidation of a new batch of aromatic hydrocarbons.

WO 9522591 discloses a process for the continuous hydrogenation of unsaturated fats, fatty acid or fatty acid esters under supercritical conditions on a shaped platinum-group metal catalyst in a solid bed constructed from an inert support and finely divided catalyst. The supercritical medium and the inert support are mixed in the free space above the catalyst in the reaction chamber in order to avoid any pressure drop in the supercritical fluid. The process is said to give considerably improved activity and selectivity in the hydrogenation reaction when compared to conventional trickle bed hydrogenation processes.

A number of patents, for example DE 3133723, DE 3133562 and U.S. Pat. No. 4,354,922 disclose the hydrocracking of coal using supercritical water as the solvent. In these patents, the hydrocarbon components of coal are degraded under the reaction conditions to produce lighter hydrocarbons hence the reaction conditions do not represent synthetically viable conditions for conventional hydrogenation reactions.

The various reaction systems described above suffer a number of disadvantages, for example waste solvent and unconsumed reactants are associated with each completed batch in a batch type process. Furthermore, in a batch type process, there is the possibility that the products obtained will be a mixture of both the kinetic reaction products and the thermodynamic reaction products unless the reaction conditions are carefully controlled to exclude one or other of these.

Although a continuous flow homogenous system overcomes the problem of formation of a mixture of kinetic and thermodynamic products because the product an be withdrawn as it is formed, this type of process suffers the disadvantage that the catalyst and the reaction products must be separated from the reaction mixture. In addition, the reactants and reaction products in this type of continuous flow process are exposed to the catalyst for a period which cannot easily be defined, in contrast to a batch type process in which the contact time is carefully controlled. Thus the starting material or products in a continuous flow reaction of this type may suffer undesirable side reactions. For the same reason, this type of continuous flow process is difficult to model and therefore does not allow an accurate prediction of the likely products, or an indication as to the likely reaction time or extent of reaction.

Previously, attempts to vary the parameters of reactions of this type have resulted in a loss of product selectivity and have not therefore been viable. For example, increasing the temperature would result in loss of hydrogen from the solution and a consequential loss in selectivity in a mass-transport-controlled reaction.

WO 96/01304 is concerned with the continuous hydrogenation of C=C double bonds in lipids to produce hydrogenated oils; the hydrogenation of triglycerides, fatty acids and methyl esters to fatty alcohols; and the hydrogenation of oxygen to hydrogen peroxide. The hydrogenation is performed under near-critical or supercritical conditions using a heterogenous catalyst. The reaction seeks to minimise the amount of transisomenisation which occurs during hydrogenation by choosing an appropriate catalyst but there is no disclosure of the control of the reaction conditions to influence the selectivity of product formation.

Accordingly, there is a need for a hydrogenation process which can be effected under conditions such that only small quantities of the organic compound and hydrogen are required in the reactor at any one time, and yet which can be used on an industrial scale for the manufacture of hydrogenated products. In addition, because undesirable side reactions or incomplete conversion of the reactants represent a waste of resources, there also remains a need for a hydrogenation process which allows careful control of the product formation and a decreased incidence of side products. Thus, the present invention seeks to provide a process in which the hydrogenation of a particular functional group and/or position of unsaturation within a compound can be effected in preference to other functional groups and/or positions of unsaturation which are also present within the compound by variation of the reaction conditions. There is also a need for a process in which wasted reaction time, and hence lost yield can be minimised by decreasing the 'downtime' of the process.

According to the present invention, there is provided a process for the selective hydrogenation of one or more functional groups in an organic compound wherein the functional group is selected from: alkene, cyclic alkene, cyclic alkane, lactone, anhydride, amide, lactam, Schiffs base, aldehyde, ketone, alcohol, nitro, hydroxylamine, nitrile, oxime, imine, azine, hydrazone, aniline, azide, cyanate, isocyanate, thiocyanate, isothiocyanate, diazonium, azo, nitroso, phenol, ether, furan, epoxide, hydroperoxide, peroxide, ozonide, arene, saturated or unsaturated heterocycle, halide, acid halide, acetal, ketal, and a selenium or sulfur containing compound, wherein the process consists of continuously hydrogenating the compound over a heterogeneous catalyst where at least one of the components, in addition to hydrogen is under supercritical or near critical conditions, and wherein or more of temperature, pressure, flow rates and hydrogen concentration are controlled for a given catalyst so as to effect selective hydrogenation of one or more functional groups and/or positions of unsaturation in the compound in preference to other functional groups and/or positions of unsaturation which are also present in the compound.

The present invention solves the above problems by effecting hydrogenation of organic compounds under conditions close to or above the supercritical point of the reaction medium in the presence of a heterogeneous catalyst in a continuous flow reactor. It will, of course, be appreciated that hydrogen may be replaced by an isotope of hydrogen (for example to effect deuteration reactions), or by a hydrogen transfer agent (for example, formic acid).

The organic compound is hydrogenated in a continuous process which comprises the steps of:

(a) admixing a supply of an inert fluid with a supply of a first organic compound and a supply of hydrogen;

(b) adjusting the temperature and pressure of the resulting admixture to pre-determined values of temperature and pressure close to or above the critical point of the fluid to produce a reaction mixture from which substantially a single desired product is formed from amongst a plurality of possible products which may be formed by hydrogenation of the first organic compound in a selective reaction, wherein the choice of the pre-determined values is dependent on which of the possible products is to be formed by reaction;

(c) exposing the reaction mixture to a heterogeneous catalyst to facilitate the selective reaction; and (d) removing the reaction mixture after reaction from the region of the catalyst and isolating the desired product by depressurisation of the reaction mixture.

The heterogeneous continuous flow system of the present invention offers a number of advantages compared with batch type systems or a homogenous continuous flow system. In particular, the present invention allows the formation of a desired end product in a selective manner by controlling one or more of: the temperature, the pressure of the reaction, by varying the catalyst used for a given set of reagents, and the flow rate through the apparatus. The factors controlling the selectivity of hydrogenation will depend on the particular reaction and in some instances the temperature or the pressure will be the controlling factor, whereas in other cases the catalyst or flow rate may be more important in determining the outcome of the reaction. Suitable conditions for a given substrate and desired product are thus determined in accordance with the present invention.

In an embodiment, the apparatus has two or more reaction zones placed in series with regard to each other, each reaction zone optionally being at a different temperature, for performing different hydrogenation reactions. Thus, a primary or secondary amine may be formed in situ by reduction of an azo, hydrazone, nitroso, nitro, oximino, hydroxylamine or nitrile group. For example, the first reaction zone may contain a catalyst for effecting reduction of a nitro compound to an amine using, for example, a palladium catalyst, and the second zone may contain, for example, a nickel catalyst for effecting reductive alkylation of the amine formed in the first zone. In this particular case, the two zones are under the same conditions of temperature and pressure with the two zones containing different catalysts to control the reaction. Similarly, a carbonyl compound may be formed in situ in the first reactor from an acetal or ketal and subsequently reacted in the second reactor.

The present invention also offers the advantage that hazardous reagents may be used without the need for a high inventory of reagent at any one time, since the organic compound and hydrogen are continuously fed to the reactor. Similarly, the product is collected continuously from the reactor and does not therefore accumulate in large quantities in the reactor where it may suffer degradation. There is also a concomitant increase in the safety of the process as compared to a batch-process when using hazardous reagents or when forming hazardous products since these materials are not usually present in sufficient quantities to represent a significant risk. Since the continuous flow process of the present invention also allows cleaner reactions to be performed than those of a corresponding batch-type process, the cost of purifying the products is reduced. Furthermore, the continuous flow process of the present invention does not require separation of the reaction product from the catalyst, as is the case in a process employing a homogenous catalyst.

The present invention has the further advantage of providing higher yields and higher throughputs than conventional methods. Whilst the actual throughputs will inevitably depend on the particular reaction employed and the size of the apparatus, throughputs of 25 mls per minute or higher are attainable using laboratory scale apparatus. Furthermore, selectivities in excess of 85% can easily be achieved using the process of the present invention.

Hydrogenation according to the present invention is performed close to or above supercritical point of the desired medium. Any fluid having a supercritical point may be employed for the process of the present invention. However, in practice the choice of fluid will depend upon the solubility of the organic compound in the fluid since a function of the supercritical or near-critical fluid is to act as a solvent for the organic compound and the hydrogen. It is also important that the reaction medium is inert with respect to the reactants and the product of the reaction in order to avoid undesirable side reactions.

The term hydrogenation in the context of the present invention is also intended to include reactions such as reductive ammination, reductive coupling and reductive alkylation, since these reactions all require a source of $H_2$ in addition to a second organic compound in order to effect reduction.

Particularly favoured media include carbon dioxide, sulphur dioxide, alkanes such as ethane, propane and butane, and halocarbons such as trichlorofluoromethane, dichlorofluoromethane, dichlorodifluoromethane, chlorotrifluoromethane, bromotrifluoromethane, trifluoromethane, and hexafluoroethane. The reaction medium may be a mixture of two or more fluids having critical points which do not require commercially unacceptable conditions of temperature and pressure in order to achieve the necessary conditions for reaction according to the present invention. For example, mixtures of carbon dioxide with an alkane such as ethane or propane, or a mixture of carbon dioxide and sulphur dioxide may be employed close to or above their theoretical critical points.

In the context of the present invention, the lower limit of the conditions suitable for supporting the hydrogenation reaction are conditions of temperature and pressure below and near the critical point. When a fluid reaches its critical point its density is substantially decreased relative to its density at its boiling point at normal pressure. Small changes in pressure near the critical point cause additional changes in density. The process will operate in the fluid at temperatures and pressures below the critical point but at which the density of the fluid is sufficient to ensure that the substrate and hydrogen are substantially in a single phase.

The upper limit of temperature and pressure is governed by limitations of the apparatus. It is also a feature of the present invention that variation of the physical conditions of the reaction may be used to control the product of the hydrogenation.

Particular organic compounds which lend themselves to the process of the present invention include the heterogeneous catalysed reduction of cyclic alkanes, arenes, alkenes, alkynes, organic halides, amines, nitro compounds, ethers, alcohols and phenols, aldehydes and ketones, sulphur-containing compounds, selenium-containing compounds, acid halides, nitriles, amides, cyclic anhydrides, anhydrides, epoxides, nitroso compounds, oximes, azides, isocyanates, isothiocyanates, diazonium compounds, hydroperoxides, peroxides, saturated or unsaturated heterocycles, and Schiff bases. Heterogeneous catalysed reductive process such as reductive coupling, reductive amination and reductive alkylation are also easily performed according to the process of the present invention. Likewise, heterogeneous catalytic hydrogenolysis of alkyl halides, aryl halides, acyl halides, alcohols and amine oxides may also be performed according to the process of the present invention. Although aliphatic compounds are more difficult to hydrogenate than aromatic compounds under the reaction conditions employed in the present invention, the hydrogenation of both aliphatic and aromatic compounds is possible according to the present invention.

Table 1 shows typical conditions for a variety of hydrogenation reactions performed according to the present invention.

TABLE 1

| Substrate | Sub. Flow [ml/min] | Solvent | Flow [l/min] | Catalyst | Substr.:$H_2$ | $P_R$ [bar] Sol. + $H_2$ | T [° C.] | Products % (analysis by GC (external standards) except when marked with # where analysis is by NMR) | | | | |
|---|---|---|---|---|---|---|---|---|---|---|---|---|
| Cyclohexene | | | | | | | | Cyclo- | | | | |
| (0.2) | 0.5–20.0 | $CO_2$ | 0.75–1.65 | 5% Pd | 1:2–4 | 120–140 | 40–320 | (98) | | | | |
| (0.3) | 0.5–2.0 | propane | 0.75 | 5% Pd, Pt | 1:2 | 60–80 | 100–170 | (96) | | | | |
| 1-Octyne* | 0.5–1.0 | $CO_2$ | 0.75 | 5% Pd | 1:4 | 120 | >40 | Octane (99.5) | | 1-Octene (0.02) | | *(0.02) |
| 1-Octene | 0.5–10.0 | $CO_2$ | 1.0 | 5% Pd | 1:2 | 120 | >40 | Octane (quant.)# | | | | |
| Acetophenone | | | | | | | | 1-phenyl-ethanol | Ethylbenzene | 1-cyclohexylethanol | Ethylcyclohexane | Cyclohexane |
| (3) | 0.5 | $CO_2$ | 1.0 | 5% Pd | 1:2 | 120 | 90 | (85) | (7) | (0) | (0) | (0) |
| (0)# | 0.5 | $CO_2$ | 1.0 | 5% Pd | 1:5 | 120 | 180 | (14)# | (41)# | (28)# | (17)# | (0)# |
| (8) | 1.0 | $CO_2$ | 1.0 | 5% Pd | 1:3 | 120 | 200 | (0) | (70) | (0) | (17) | (0) |
| (6) | 0.5 | $CO_2$ | 1.0 | 5% Pd | 1:6 | 120 | 300 | (0) | (4) | (1) | (88) | (1) |
| Benzaldehyde | | | | | | | | Benzylalcohol | Toluene | cyclohexylmethanol | Methylcyclohexane | Cyclohexane |
| (0)# | 0.5 | $CO_2$ | 1.0 | 5% Pd | 1:2 | 120 | 95 | (92)# | (8)# | (0)# | (0)# | (0)# |
| (0)# | 0.5 | $CO_2$ | 1.0 | 5% Pd | 1:4 | 120 | 140 | (18)# | (77)# | (4)# | (1)# | (0)# |
| (0)# | 0.5 | $CO_2$ | 1.0 | 5% Pd | 1:6 | 120 | 180 | (22)# | (59)# | (10)# | (7)# | (1)# |
| (0)# | 0.5 | $CO_2$ | 1.0 | 5% Pd | 1:8 | 120 | 270 | (1)# | (22)# | (3)# | (40)# | (25)# |

| Substrate | Sub. Flow [ml/min] | Solvent | Flow [l/min] | Catalyst | Substr.:$H_2$ | $P_R$ [bar] (Sol. + $H_2$) | T [° C.] | Products % (analysis by GC (external standards) except when marked with # where analysis is by NMR) | | | |
|---|---|---|---|---|---|---|---|---|---|---|---|
| Nitrobenzene | | | | | | | | Aniline | Aminocyclohexane | Dicyclohexylamine | Cyclohexane |
| (0) | 0.5 | propane | 0.75 | 1% Pd | 1:6 | 80 | 150–200 | (97) | (0) | (0) | (0) |
| (3) | 0.3 | propane | 0.75 | 5% Pd | 1:9 | 80 | 200–250 | (9) | (29) | (58) | (1) |
| 1,2-(Methylenedioxy)-4-nitrobenzene | | Starting material dissolved in a mixture of MeOH and THF, flow of solution: 10 ml min$^{-1}$ | | | | | | 1,2-(Methylenedioxy)-4-aminobenzene | | | |

TABLE 1-continued

| | Flow | Fluid | | Catalyst | Ratio | Temp | Pressure | Product 1 | Product 2 | Product 3 | Product 4 |
|---|---|---|---|---|---|---|---|---|---|---|---|
| 0.8 mmol min$^{-1}$ 2,4-Difluoro- | | $CO_2$ | 1.0 | 1% Pd | 1:6 | 140 | 90 | (quantitative)[#] 2,4-Difluoroaniline | | | |
| (26)[#] Phenylacetonitrile | 0.5 | $CO_2$ | 1.0 | 1% Pd | 1:2 | 120 | 130 | (74)[#] Tris-2-phenylethylamine | Ethylbenzene | Ethylcyclohexane | |
| (0)[#] | 0.5 | propane | 1.0 | 5% Pd | 1:4 | 120 | 130 | (57)[#] | (36)[#] | (7)[#] | |
| (2)[#] | 0.5 | propane | 1.0 | 5% Pd | 1:6 | 120 | 160 | (24)[#] | (58)[#] | (16)[#] | |
| (0)[#] Propylene oxide | 0.5 | propane | 1.0 | 5% Pd | 1:8 | 120 | 200 | (4)[#] 2-Propanol | (55)[#] 1-Propanol | (41)[#] Acetone | Propanal |
| (42)[#] | 0.5 | $CO_2$ | 1.0 | 5% Pd | 1:2 | 120 | 120 | (49)[#] | (5)[#] | (4)[#] | (0)[#] |
| (17)[#] Cyclohexene oxide | 1.0 | $CO_2$ | 1.0 | 5% Pd | 1:3 | 120 | 250 | (22)[#] Cyclohexanol | (42)[#] Cyclohexanone | (15)[#] Cyclohexane | (4)[#] Dicyclohexylether |
| (6)[#] Cyclohexanone | 0.5 | $CO_2$ | 1.0 | 5% Pd | 1:2 | 120 | 200 | (80)[#] Cyclohexanol | (9)[#] Phenol | (1)[#] | (4)[#] |
| (83)[#] Isophorone | 0.5 | $CO_2$ | 0.65 | 3% Ru | 1:1.5 | 120 | 300 | (17)[#] | (0)[#] 3,5,5-trimethylcyclohexanol | 1,1,3-trimethylcyclohexane | |
| (0) | 0.5–2.0 | $CO_2$ | 0.78 | 5% Pd | 1:2 | 120 | 140–200 | (100) | (0) | (0) | |
| | 1.0 | $CO_2$ | 0.78 | 5% Pd | 1:3 | 200 | 300 | 58 | 22 | 14 | |
| Cyclohexanol | | | | | | | | Cyclohexanone | Cyclohexane | Benzene | |
| (25)[#] meta-Cresol | 0.5 | $CO_2$ | 0.65 | 5% Pd | 1:3 | 120 | 400 | (12)[#] 3-Methylcyclohexanone | (60)[#] 3-Methylcyclohexanol | (3)[#] Methylcyclohexane | Toluene |
| (20) | 0.5 | $CO_2$ | 0.65 | 5% Pd | 1:2 | 120 | 250 | (65) | (14) | (<0.5) | (<0.5) |
| (0) | 0.5 | $CO_2$ | 0.65 | 5% Pd | 1:5 | 120 | 250 | (17) | (74) | (5) | (0) |
| (2) Propionaldehyde | 0.5 | $CO_2$ | 0.65 | 5% Pd | 1:6 | 120 | 400 | (5) 1-Propanol | (4) | (74) unidentified product | (15) |
| (32) 2-Butanone oxime | 0.5–1.0 | $CO_2$ | 1.0 | 5% Ru | 1:2.5 | 120 | 150 | (35) 2-Aminobutane | 2-Butanone | (33) 2-Butanol | |
| (4) | 0.5 | propane | 0.75 | 5% Pt | 1:2 | 80 | 150–170 | (86) | (10) | (<1) | |

Flow = Flow rate of fluid in l/min at 20° C. and 1 atm, as determined by flow meter
Catalyst = Deloxan catalyst as presented in Table 2

It is apparent from Table 1 that for a given reaction medium, variation of the heterogeneous catalyst and/or the reaction conditions allows control of the desired end product where there is more than one possible product. Also, in the case of a given catalyst it can be seen that the process of the present invention enables the hydrogenation of a particular functional group and/or position of unsaturation within a compound to be performed selectively when other functional groups and/or positions of unsaturation are also present in the compound.

Thus, nitrobenzene may be reduced to aniline, aminocyclohexane or dicyclohexylamine depending on the predetermined reaction conditions which are used. By changing the temperature of hydrogenation of nitrobenzene under conditions of excess hydrogen it is possible to influence the selectivity. The reaction is kinetically controlled under these conditions and does not depend on mass transport effects. Similarly, alkynes such as octyne can be selectively hydrogenated in the process of the present invention by varying the conditions of the reaction.

Since temperature, pressure and flow rate are parameters which are readily controlled by an operator, the present invention enables a particular product to be obtained in good yield in a process which is commercially viable on account of its safety and ease of use. Product formation may be monitored in situ by means of IR spectrometry using a suitably positioned high pressure IR cell.

Figure 2:
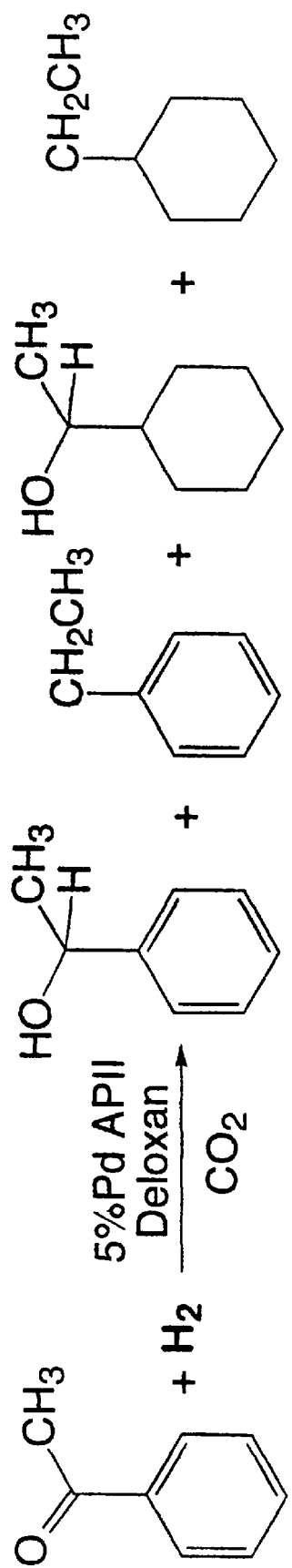
Figure 3:
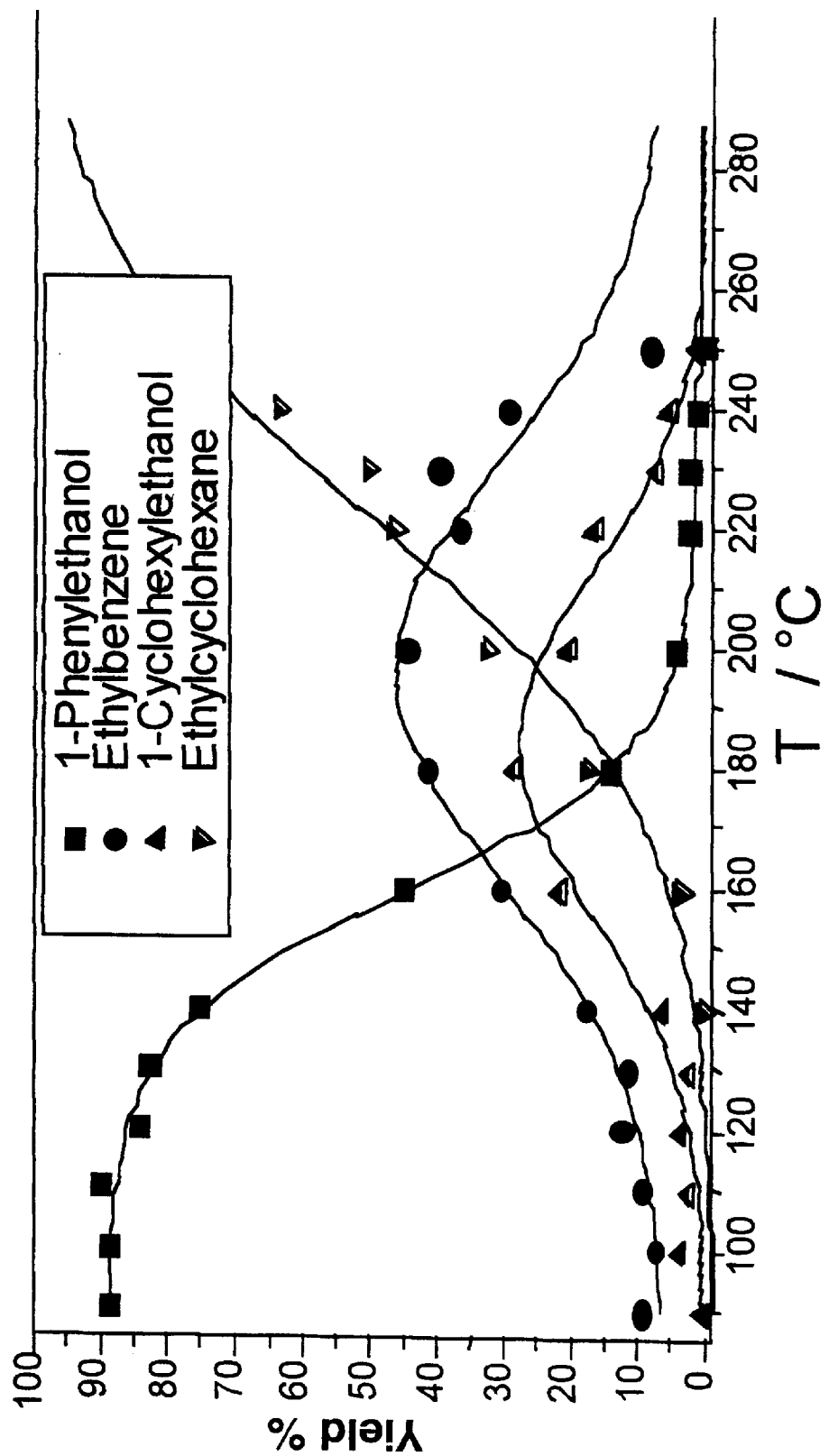
Figure 4:
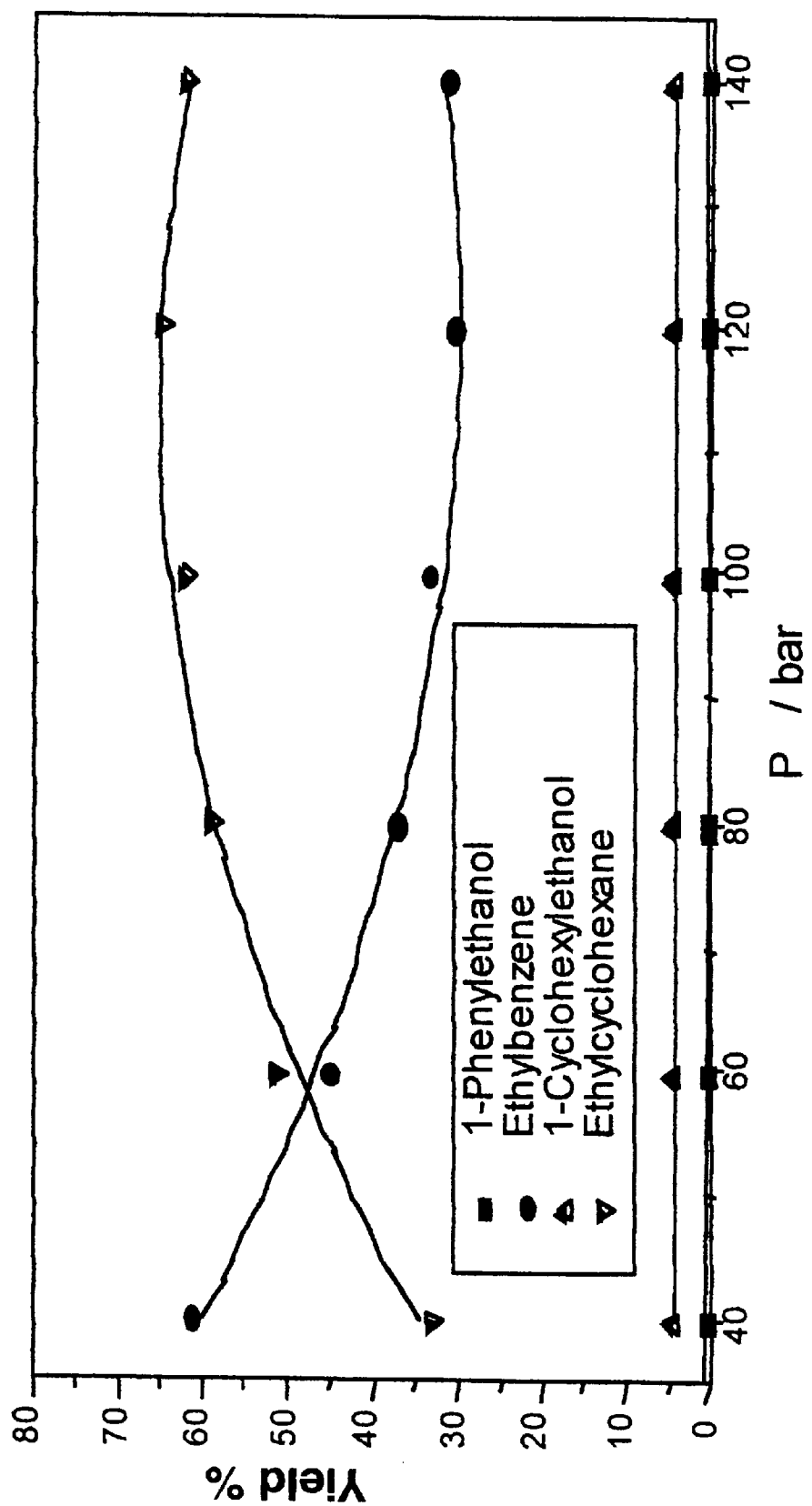
Figure 5:
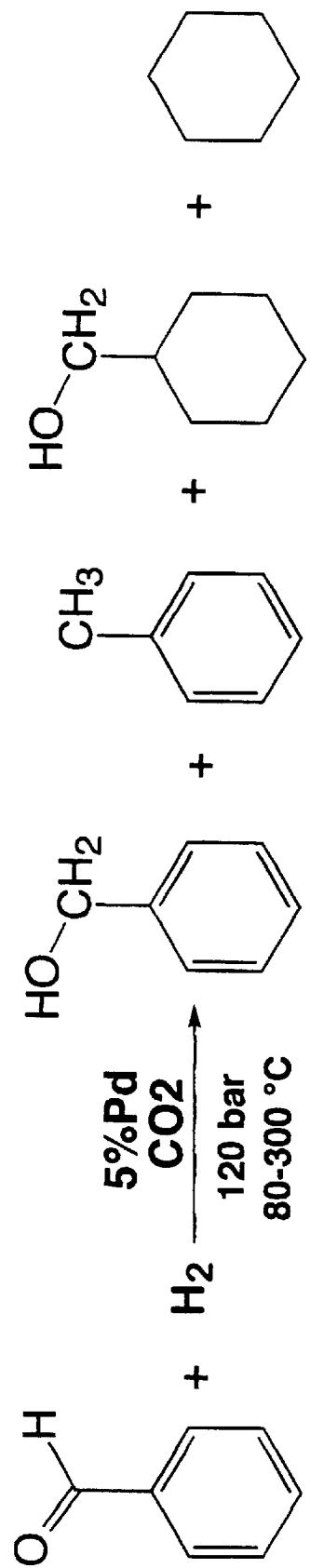
Figure 6:
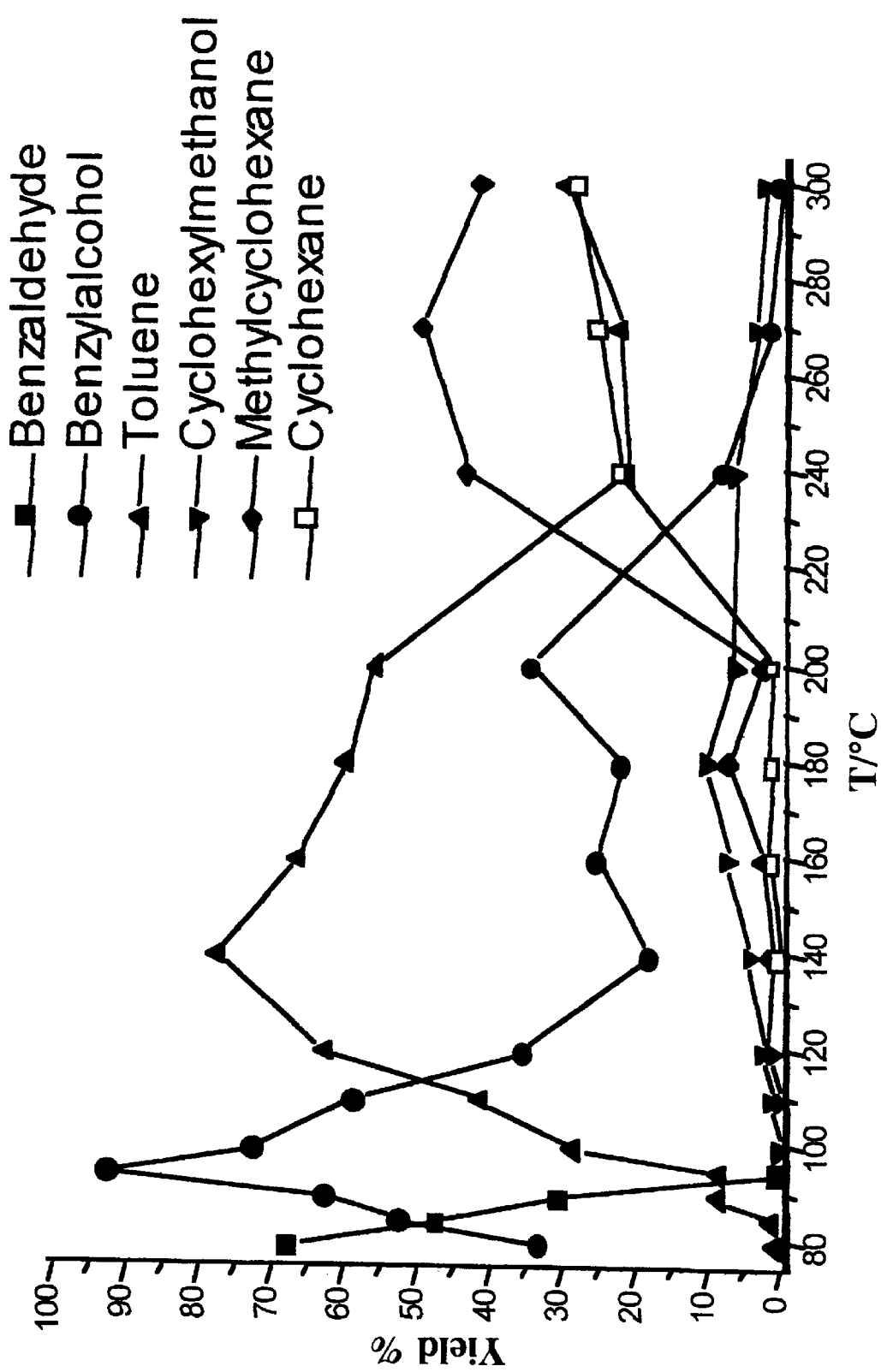
Figure 7:
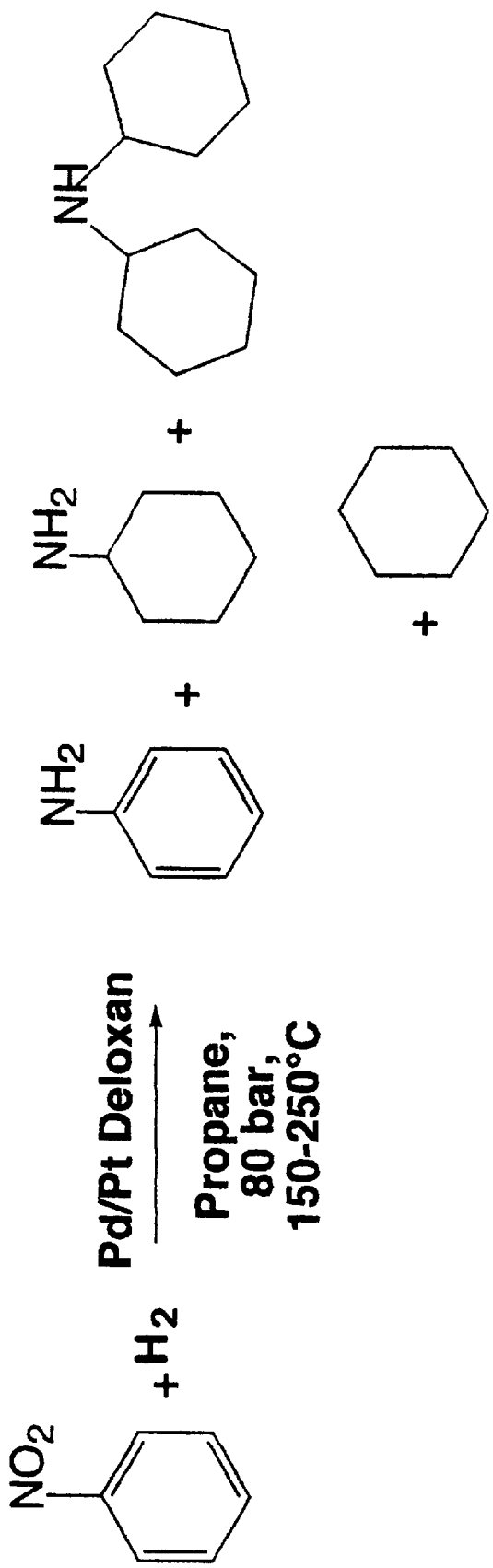

The present invention will now be described by way of example only with reference to FIGS. 1 to 7, in which:

FIG. 1 which is a schematic diagram of a continuous flow reactor according to the present invention, FIG. 2 shows the possible hydrogenation products acetophenone, FIG. 3 shows the relative proportions of the hydrogenation products of acetophenone at various temperatures with increasing hydrogen, FIG. 4 shows the relative proportions of the hydrogenation products of acetophenone at various pressures, FIG. 5 shows the possible hydrogenation products of benzaldehyde, FIG. 6 shows the relative proportions of the hydrogenation products of benzaldehyde at various temperatures with increasing hydrogen, and FIG. 7 shows the possible hydrogenation products of nitrobenzene.

The organic compound 1, dissolved in an appropriate solvent if it is a solid, is pumped into mixer 2 which may include a stirrer (not shown) where it is mixed with fluid 3 which has been delivered from reservoir 4 via pump 5 to mixer 2. Mixing of organic compound 1 and fluid 3 may equally be effected without he use of a stirrer. Hydrogen 6 is delivered from reservoir 7 via compressor 8 and a dosage unit (e.g. a 6-way injection valve) 9 to mixer 2. The hydrogen pressure is typically set to a pressure of 200 to 220 bar inclusive by means of conventional pressure regulating apparatus. Addition of dissolved organic compound 1 and/or hydrogen 6 may be continuous or may occur continuously in a step-wise manner. The hydrogen is added via a switching valve or similar control means to give the required ratio of hydrogen to the organic compound. The ratio of hydrogen to organic compound is chosen according to the reaction to be used and is typically in the range from 1.0:1.0, to 3.0:1.0, inclusive, equivalents of $H_2$ per reaction and is preferably set at 1.1:1.0 or 1.3:1.0 equivalents of $H_2$ per reaction for optimum results.

The temperature and/or pressure of the mixture of organic compound 1, fluid 3 and hydrogen 6 is adjusted in mixer 2 to a temperature and pressure close to or above the critical point of fluid 3 as required. Heating means or cooling means 10 is provided in mixer 2 for this purpose. Equally, this may be achieved via heating/cooling the reactor or a combination of both. The mixture is then passed into reactor 11 which contains a catalyst (not shown) fixed on a suitable support. Suitable catalysts compose a carrier formed from an organosiloxane-polycondensate, an organosiloxanamine-copolycondensate or polymeric secondary and/or tertiary organosiloxanamine combinations, a metal selected from platinum, nickel palladium or copper or a mixture thereof, and optionally a promoter. After an appropriate residence time in reactor 11 fluid 3, which contains product 12, is passed into pressure reduction unit 13 and the product is removed via take off tap 14 after passing through pressure reduction unit 13. The flow rate of the reactants through reactor 11 is controlled by a valve (not shown) in pressure reducer 13. The quantity of materials consumed in the reaction and the rate of reaction are determined by the temperature, the feed rate of organic compound 1 into fluid 3 and the flow rate of fluid 3. Fluid 3, together with any unconsumed hydrogen, is vented through relief pipe 15 for subsequent recycling or to the atmosphere.

The parameters of a typical reaction might involve a system pressure of 60 to 140 bar (this will, of course, depend in part on the reaction media), a flow rate of the substrate of 0.5 to 20.0 ml/min, a reactor temperature of 40 to 360° C. (again, this will depend in part on the reaction media) and a flow rate of the supercritical or near critical fluid of 0.65 to 1.65 l/min; however, these parameters do not imply limitations to within the respective ranges.

EXAMPLE 1

Hydrogenation of Acetophenone

Hydrogenation of acetophenone leads to a variety of products, as illustrated in FIG. 2 below. Each of the products can be obtained selectively by appropriate choice of the reaction conditions.

The effect of the reaction temperature on the selectivity of the reaction in $CO_2$ is demonstrated in FIG. 3. The pressure of the reaction was maintained at 120 bar and the catalyst was APII 5% Pd Deloxan having a particle size 0.3 to 0.8 mm, supplied by Degussa.

The effect of the reaction pressure on the selectivity of the same reaction in $CO_2$ at a constant temperature of 240° C. and using the same catalyst is illustrated in FIG. 4.

EXAMPLE 2

Hydrogenation of Benzaldehyde

Benzaldehyde can be hydrogenated to more than one product, as illustrated in FIG. 5, and FIG. 6 shows the variation of product selectivity with temperature at a pressure of 120 bar and using an APII 5% Pd Deloxan catalyst having a particle size of 0.3 to 0.8 mm, supplied by Degussa.

EXAMPLE 3

Hydrogenation of Nitrobenzene

Nitrobenzene may be hydrogenated to a number of products, as illustrated in FIG. 7.

Table 2 illustrates how the selectivity of the reaction is influenced by small differences in the catalyst at a constant pressure of 80 bar.

TABLE 2

| Catalyst | Temperature ° C. | Aniline % | Cyclohexylamine % | Dicyclohexylamine % | Cyclohexane % |
| --- | --- | --- | --- | --- | --- |
| APII 1% Pd Deloxan | 150–200 | 97 | 0 | 0 | 0 |
| E 8550 P/D 5% Pd Deloxan | 200–250 | 9 | 29 | 58 | 1 |
| APII 5% Pt Deloxan | 200 | 46 | 13 | 4 | 28 |

Finally, it should be noted that whilst the experiments described herein represent the most appropriate conditions for those reactions at the present time, it is nevertheless envisaged that the yields and selectivities of these reactions may be enhanced further following the principles of the invention described herein.

What is claimed is:

1. A process for achieving selective hydrogenation of one or more functional groups in an organic compound substrate to produce a selected hydrogenation product, wherein the substrate is an organic compound being, or having a group in its molecule, selected from: alkene, cyclic alkene and cyclic alkane, lactone, anhydride, amide, lactam, Schiff's base, aldehyde, ketone, alcohol, nitro, hydroxylamine, nitrile, oxime, imine, azine, hydrazone, aniline, azide, cyanate, isocyanate, thiocyanate, isothiocyanate, diazonium, azo, nitroso, phenol, ether, furan, epoxide, hydroperoxide, peroxide, ozonide, arene, saturated or unsaturated heterocycle, halide, acid halide, acetal, ketal, and a selenium or sulfur containing compound, wherein the process comprises:

continuously supplying, in a preliminary stage, the compound to a heterogeneous catalyst to pass thereover and be removed from the catalyst in a continuous flow procedure with at least one component, in addition to hydrogen, being under supercritical or under near-critical conditions, near-critical conditions being conditions below supercritical at which density of a fluid is sufficient to ensure that reactants are substantially in a single phase, varying one or more of temperature, pressure, flow rates and hydrogen concentration that, for the catalyst, define a set of conditions, to obtain hydrogenation products differing as to identity and/or proportions of different reaction products in accordance with a prevailing set of conditions, and subsequently applying a selected set of conditions to obtain only a selected hydrogenation product in accordance with the selected set of conditions.

2. A process according to claim 1, wherein all the substrate and hydrogen are in a homogeneous single phase with or without an additional solvating fluid.

3. A process according to claim 1, wherein the selective hydrogenation is hydrogenolysis.

4. A process according to claim 1, wherein the selective hydrogenation reaction is reductive alkylation of primary and secondary amines or ammonia.

5. A process according to claim 4, wherein the primary or secondary amine is formed in situ before further reaction.

6. A process according to claim 1, wherein the selective hydrogenation reaction is reductive amination of aldehydes, ketones and phenols.

7. A process according to claim 6, wherein a carbonyl compound is formed in situ before further reaction with an amine.

8. A process according to claim 1, wherein the organic compound is an aromatic compound.

9. A process according to claim 1, wherein a supercritical component is selected from carbon dioxide, an alkane, an alkene, ammonia, a halocarbon, or a mixture of any of these.

10. A process according to claim 1, wherein a supercritical component is selected from carbon dioxide, propane, or a mixture thereof.

11. A process according to claim 1, wherein the catalyst is a supported metal catalyst.

12. A process according to claim 1, wherein the catalyst comprises:

a carrier formed from a group selected from an organosiloxanepolycondensate, an organosiloxanamine-copolycondensate and polymeric secondary and/or tertiary organosiloxanamine combinations; and a metal selected from platinum, nickel, palladium, copper and combinations thereof.

13. A process according to claim 1, wherein a source of hydrogen is selected from an isotope of hydrogen and a hydrogen transfer reagent.

14. A process according to claim 2, wherein the selective hydrogenation is hydrogenolysis.

15. A process according to claim 2, wherein the selective hydrogenation reaction is reductive alkylation of primary and secondary amines or ammonia.

16. A process according to claim 15, wherein the primary or secondary amine is formed in situ before further reaction.

17. A process according to claim 2, wherein the selective hydrogenation reaction is reductive amination of aldehydes, ketones and phenols.

18. A process according to claim 17, wherein a carbonyl compound is formed in situ before further reaction with an amine.

19. A process according to claim 12, wherein the catalyst further comprises a promoter.

* * * * *